(12) United States Patent
Buess et al.

(10) Patent No.: US 11,154,219 B2
(45) Date of Patent: Oct. 26, 2021

(54) HOLDING DEVICE FOR A BREATHING TUBE AND METHOD FOR READING OUT A CODING ON A SURFACE OF A BREATHING TUBE

(71) Applicant: ndd Medizintechnik AG, Zurich (CH)

(72) Inventors: Christian Buess, Horgen (CH); Erich Kleinhappl, Waedenswil (CH)

(73) Assignee: ndd Medizintechnik AG, Zurich (CH)

( * ) Notice: Subject to any disclaimer, the term of this patent is extended or adjusted under 35 U.S.C. 154(b) by 286 days.

(21) Appl. No.: 15/979,952

(22) Filed: May 15, 2018

(65) Prior Publication Data

US 2018/0333077 A1    Nov. 22, 2018

(30) Foreign Application Priority Data

May 16, 2017   (EP) .................................... 17171303

(51) Int. Cl.
| | |
|---|---|
| *A61B 5/097* | (2006.01) |
| *A61B 5/08* | (2006.01) |
| *A61B 5/00* | (2006.01) |
| *A61B 5/087* | (2006.01) |
| *A61L 29/04* | (2006.01) |
| *A61L 29/06* | (2006.01) |
| *A61B 90/00* | (2016.01) |
| *G01B 11/14* | (2006.01) |

(52) U.S. Cl.
CPC ............ *A61B 5/097* (2013.01); *A61B 5/0059* (2013.01); *A61B 5/08* (2013.01); *A61B 5/082* (2013.01); *A61B 5/087* (2013.01); *A61L 29/041* (2013.01); *A61L 29/043* (2013.01); *A61L 29/06* (2013.01); *A61B 2090/0811* (2016.02); *G01B 11/14* (2013.01)

(58) Field of Classification Search
None
See application file for complete search history.

(56) References Cited

U.S. PATENT DOCUMENTS

| 5,419,326 A | 5/1995 | Harnoncourt |
|---|---|---|
| 2005/0267386 A1 | 12/2005 | Copelan |
| 2007/0261698 A1 | 11/2007 | Palatnik |
| 2010/0036272 A1 | 2/2010 | Mace et al. |
| 2015/0165185 A1 | 6/2015 | Cohen et al. |
| 2015/0272475 A1 | 10/2015 | Buess |

(Continued)

FOREIGN PATENT DOCUMENTS

| CN | 1228015 A | 9/1999 |
|---|---|---|
| CN | 104970795 A | 10/2015 |

(Continued)

OTHER PUBLICATIONS

European Patent Office, Office Action Issued in Application No. 17171303.5, dated Feb. 1, 2019, Netherlands, 9 pages.

*Primary Examiner* — Kaylee R Wilson
*Assistant Examiner* — Jay B Shah
(74) *Attorney, Agent, or Firm* — McCoy Russell LLP

(57) ABSTRACT

A holding device for a breathing tube for use in lung function diagnostics is disclosed. This holding device consists of a material that is transparent for light having a wavelength in a first wavelength range but nontransparent for light having a wavelength in a second wavelength range. In other aspects, a lung function diagnostics device comprising such a holding device and a method for reading out a coding on a surface of a breathing tube for use in lung function diagnostics are disclosed.

16 Claims, 6 Drawing Sheets

(56) References Cited

U.S. PATENT DOCUMENTS

| | | |
|---|---|---|
| 2015/0307688 A1 | 10/2015 | Kitao et al. |
| 2016/0053081 A1 | 2/2016 | Harada et al. |
| 2016/0128608 A1 | 5/2016 | Buess et al. |
| 2017/0044375 A1 | 2/2017 | Kitao et al. |

FOREIGN PATENT DOCUMENTS

| | | |
|---|---|---|
| CN | 105158814 A | 12/2015 |
| CN | 105581796 A | 5/2016 |
| CN | 106029158 A | 10/2016 |
| EP | 2940495 A1 | 11/2015 |
| EP | 3017760 A1 | 5/2016 |
| WO | 9324810 A1 | 12/1993 |
| WO | 9748338 A1 | 12/1997 |
| WO | 2016172555 A1 | 10/2016 |

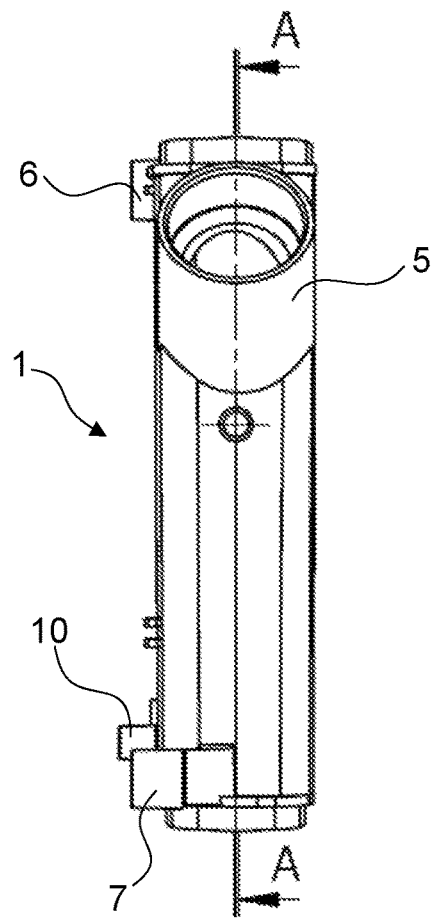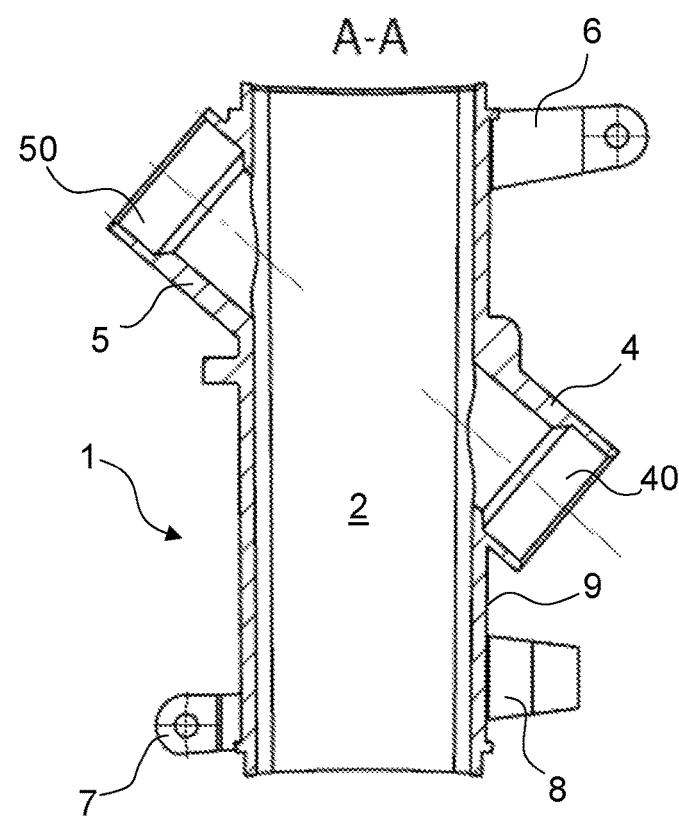
FIG 1E
FIG 1F

HOLDING DEVICE FOR A BREATHING TUBE AND METHOD FOR READING OUT A CODING ON A SURFACE OF A BREATHING TUBE

CROSS-REFERENCE TO A RELATED APPLICATION

This application claims priority of European patent application 17 171 303.5-1657, filed on May 16, 2017, the entire contents of which is hereby incorporated by reference in its entirety for all purposes.

BACKGROUND

The instant disclosure relates to a holding device for a breathing tube for use in lung function diagnostics to a lung function diagnostics device equipped with such a holding device, to a novel use of a selectively transparent material, and to a method for reading out a coding on the surface of a breathing tube.

It is common in lung function diagnostics to use breathing tubes (also known as flow tubes) to measure the gas inhaled and/or exhaled by a patient. EP 3 017 760 A1 describes such a breathing tube. This European patent application also describes a comb-like indicator on the breathing tube serving as coding element. It is furthermore described in this European patent application to read out the comb-like structure by a light source and a corresponding detector.

It has been observed that the reliability of reading out such a comb-like structure or a comparable coding element on a surface of a breathing tube is often lower than desired.

SUMMARY

It is an object of the instant disclosure to provide a holding device for a breathing tube that is particularly appropriate to hold a breathing tube having a coding element like a comb-like coding structure on its outer surface, wherein the holding element serves for a higher reliability of reading out this coding element. Furthermore, such a holding device shall be manufactured in a particularly simple manner.

This object is achieved by a holding device having the features explained in the following. Such a holding device serves to hold a breathing tube that is to be used in lung function diagnostics. Thereby, the holding device comprises a material that is transparent for light having a wavelength in a first wavelength range but nontransparent for light having a wavelength in a second wavelength range (selectively transparent material). Thereby, the first wavelength range differs from the second wavelength range. Due to this selectively transparent material, light having a wavelength in the first wavelength range can be radiated through the holding device onto a breathing tube which is arranged within the holding device so that a coding structure on the surface of the breathing tube can be read out by the aid of the light. By such an arrangement, it is no longer necessary to provide a breakthrough in the holding device that can be passed by any light. Rather, the material of the holding device is chosen to be transparent for the first wavelength range at least in the region in which the light shall pass through the holding device to be able to read out a coding structure on a breathing tube inserted into the holding device. By such a design of the holding tube, the influence of stray light passing through the holding device towards a light detector is decreased. This in turn increases the sensitivity and/or selectivity of a corresponding detecting device so that the overall readout process becomes much more reliable.

The term "transparent" is to be understood such that a material is to be considered as transparent if at least 75%, in particular at least 80%, in particular at least 85%, in particular at least 90%, in particular at least 95%, in particular at least 97%, in particular at least 99%, in particular 100% of light radiated onto the material passes the material, i.e. if has a transparency of the before-mentioned percentages.

The term "nontransparent" is to be understood such that a material is to be considered as nontransparent if less than 25%, in particular less than 20%, in particular less than 15%, in particular less than 10%, in particular less than 5%, in particular less than 3%, in particular less than 2%, in particular lesser than 1%, in particular 0% of light radiated onto the material passes the material.

The term "lung function diagnostics" refers to any kind of the analysis of breath gas (i.e., the analysis of gas inhaled or exhaled by a person) to determine the lung function of a patient, in particular applications of spirometry, gas washout measurements, gas dilution measurements, or gas diffusion measurements. Typical parameters determined by lung function diagnostics are forced vital capacity (FVC), forced expiratory volume in 1 second (FEV1), FEV1/FVC ratio (FEV1%), forced expiratory flow (FEF), forced inspiratory flow 25-75% or 25-50%, peak expiratory flow (PEF), tidal volume (TV), total lung capacity (TLC), diffusing capacity (DLCO), maximum voluntary ventilation (MVV), functional residual capacity (FRC), and/or lung clearance index (LCI). The instantly described holding device is intended to hold breathing tubes to be used for determining any of these parameters in spirometry or to be used for any other kinds of lung function diagnostics without specific limitation.

In an embodiment, the holding device entirely consists of the selectively transparent material. This enables a particularly simple manufacturing of the holding device since it can then be manufactured in a single process step, e.g., by injection molding. Other appropriate manufacturing techniques can also be applied. Since the whole holding device can be made from a single material, no specific limitations regarding the manufacturing process are necessary.

In an embodiment, the first wavelength range comprises wavelengths of at least 600 nm (i.e. 600 nm and above), in particular at least 650 nm, in particular at least 700 nm, in particular at least 750 nm, in particular at least 800 nm, in particular at least 850 nm, in particular at least 900 nm, in particular at least 950 nm, in particular at least 1000 nm. An appropriate first wavelength range is a range of 600 nm to 1000 nm, in particular 650 nm to 950 nm, in particular 700 nm to 900 nm, in particular 750 nm to 850 nm, in particular 800 nm to 900 nm. In an embodiment, the first wavelength range comprises wavelengths of infrared light, i.e., the material is transparent for infrared light.

It is appropriate if the first wavelength range is comparatively narrow so as to allow a transmission of specific, narrow-banded light. In an embodiment, the first wavelength range has a spectral width of not more than 200 nm, in particular not more than 150 nm, in particular not more than 100 nm, in particular not more than 75 nm, in particular not more than 50 nm, in particular not more than 30 nm. An appropriate spectral width for the first wavelength range is a spectral width of 30 nm to 200 nm, in particular 50 nm to 150 nm, in particular 75 nm to 100 nm.

In an embodiment, the second wavelength range comprises wavelengths of less than 600 nm (i.e., lower than 600 nm), in particular of less than 550 nm, in particular of less than 500 nm, in particular of less than 450 nm, in particular of less than 400 nm. An appropriate second wavelength range is a range of 300 nm to 600 nm, in particular 350 nm to 550 nm, in particular 400 nm to 500 nm.

It is appropriate if the second wavelength range is comparatively broad so as to filter a broad range of potentially disturbing stray light. In an embodiment, the second wavelength the range has a spectral width of at least 200 mm, in particular at least 250 nm, in particular at least 300 nm, in particular at least 350 nm, in particular at least 400 nm, in particular at least 450 nm, in particular at least 500 nm. An appropriate spectral width for the second wavelength range is a spectral width of 200 nm to 500 nm, in particular 250 nm to 450 nm, in particular 300 nm to 400 nm.

In an embodiment, the first wavelength the range comprises wavelengths above 700 nm, wherein the second wavelength range comprises wavelengths below 700 nm.

In an embodiment, the holding device has an inner main space. Thereby, a breathing tube can be inserted into this inner main space and can be removed from the inner main space after the measurement has been done. This makes it particularly simple to exchange breathing tubes after use, e.g. for hygienic reasons. One-piece breathing tubes (without exchangeable mouth piece) are directly contacted by a patient's mouth so that each breathing tube is regularly used for a single patient.

In an embodiment, the holding device comprises a main body surrounding the inner main space. Furthermore, a first side body extending laterally from the main body on a first side and a second side body extending laterally from the main body on a second side are provided. Thereby, the first side is opposite to the second side. The first side body surrounds a first inner side space and the second side body surrounds a second inner side space. The first inner side space serves for housing a first ultrasonic transceiver, and the second inner side space serves for housing a second ultrasonic transceiver. By such an arrangement of the holding device, ultrasonic measurements of gas flowing through a breathing tube inserted into the holding device can be performed in a particularly simple manner.

In an embodiment, the main body is made from a selectively transparent material. In another embodiment, both the main body and the first and second side bodies are made from the same selectively transparent material.

In an embodiment, the holding device comprises a fitting that extends away from a lateral portion of the main body of the holding device. Thereby, the fitting has a free end which is arranged in a first plane. This first plane extends in an angle of 30° to 120°, in particular 40° to 110°, in particular 50° to 100°, in particular 60° to 90°, in particular 70° to 80° with respect to a second plane in which the lateral portion of the main body extends (from which lateral portion, in turn, the fitting extends). Thereby, the fitting serves for guiding an infrared light beam in its interior such that the light beam changes its direction within the fitting.

In an embodiment, the first plane is approximately perpendicular (i.e., in an angle of 80° to 100°, in particular 85° to 95°, in particular 88° to 92°, in particular 89° to 91° and very particular 90°) to the second plane.

The angle between the first plane and the second plane is chosen such that the free end of the fitting reaches, in the installed state of the holding device within a lung function diagnostics device, into the light emitting area (light cone) of a light source so that light emitted from that light source can be guided through the fitting towards and through the main body of the holding device. If a light source is chosen that emits light in an upward direction, an approximately perpendicular arrangement between the first plane and the second plane is particularly appropriate to allow the fitting to guide light from the light source towards the main body of the holding device. If a light source is chosen which emits light in a broader angular range, a different angular arrangement between the first plane and the second plane can be chosen likewise.

Since the fitting connects two areas with each other that are located angularly, in particular approximately perpendicular, to each other, the fitting is able to also guide a light beam in its interior in an angled way. Since the light beam does not necessarily need to leave the fitting perpendicularly to the second plane, the overall angle, in which the light beam is guided within the fitting, does not necessarily need to correspond to the angle in which the first plane and the second plane are arranged to each other. Rather, the fitting is appropriate, in an embodiment, to guide a light beam in its interior in such a way that an angle between a line in an entry direction of the light beam and a line in an exit direction of the light beam guided within the fitting is in a range of from between 30° to 90°, in particular from 35° to 85°, in particular from 40° to 80°, in particular from 45° to 75°, in particular from 50° to 70°, in particular from 55° to 65°, in particular from 60° to 90°.

In an embodiment, the fitting has a curved surface. Such a curved surface is appropriate to allow guiding a light beam in the interior of the fitting.

In an embodiment, the curved surface comprises at least two sections with different curvatures. Then, a light beam entering the fitting is reflected in the first section (having a first curvature) in a first angle towards the second section (having a second curvature) and is there reflected in a second angle. Thereby, the second angle can be the same as the first angle or can be different from the first angle. It is furthermore possible that a light beam is reflected more than twice within the fitting. It is in particular ensured that a light beam guided through the fitting is reflected in each section of the fitting having a curvature which deviates from the curvature of another section of the same fitting.

In an embodiment, the holding device comprises a lens that is integrally formed on the surface of the holding device. Such a lens is typically manufactured from the same material as the rest of the holding device, i.e. a selectively transparent material. Thus, it is not necessary to insert a lens made from another material into the holding device. Rather, the lens can be manufactured together with the main body of the holding device in a single manufacturing step. The lens serves for focusing light being guided through the lens towards the sensor (detecting device) arranged outside the holding device.

In an embodiment, the lens faces towards the first plane i.e., the plane in which a light entry surface of the fitting is arranged.

In an embodiment, the selectively transparent material comprises at least one base material chosen from the group consisting of polycarbonates, acrylonitrile butadiene styrene, polystyrene, poly(methyl methacrylate), polyethylene terephthalate, polyethylene terephthalate glycol, copolymers of polystyrene and polyethylene terephthalate glycol, cellulose esters such as cellulose acetate butyrate, as well as blends and copolymers of these base materials. These materials exhibit a good overall light transparency, are insensitive to scratches and are stable enough so that the holding device can be produced with a small wall thickness but is still stable enough to securely house a breathing tube.

To achieve a selective light transparency of the material from which the holding device is made, the selectively transparent material additionally comprises a coloring agent having a filter effect for light having a specific wavelength. Then, the selectively transparent material is light nontransparent for light having a wavelength which is filtered by the coloring agent and is light transparent for light having a wavelength lying outside this range. Appropriate coloring agents are, e.g., the coloring agents disclosed in US 2015/0307688 A1, US 2016/0053081 A1, US 2017/0044375 A1, and EP 2 940 495 A1. These patent applications are herewith incorporated by reference for the purpose of disclosing appropriate coloring agents. Depending on the base material used, a further appropriate coloring agent is the coloring agent marketed by Clariant under the name "Polysynthren Black H". Further appropriate coloring agents are 1-hydroxy-4-(p-toluidino)-anthraquinon (CAS no. 81-48-1), 4-[(1,5-dihydro-3-methyl-5-oxo-1-phenyl-4H-pyrazol-4-ylidene)methyl]-2,4-dihydro-5-methyl-2-phenyl-3H-pyrazol-3-one (CAS no. 4701-90-3), and mixtures thereof.

Appropriate concentrations of the coloring agent in the selectively transparent material are 1 to 20 percent by weight (% (w/w)), in particular 1.5 to 19% (w/w), in particular 2 to 18% (w/w), in particular 2.5 to 17% (w/w), in particular 3 to 16% (w/w), in particular 3.5 to 15% (w/w), in particular 4 to 15% (w/w), in particular 4.5 to 14% (w/w), in particular 5 to 13% (w/w), in particular 5.5 to 12% (w/w), in particular 6 to 11% (w/w), in particular 6.5 to 10% (w/w), in particular 7 to 9% (w/w), in particular 7.5 to 8.5% (w/w).

In an aspect, the instant disclosure also relates to a lung function diagnostics device that is characterized by a holding device according to the preceding explanations.

In an embodiment, the lung function diagnostics device additionally comprises a circuit board having a light source appropriate to emit light having a wavelength in a first wavelength range and the detecting device is appropriate to detect the light having a wavelength in the first wavelength range. Thereby, the light source and the detecting device face the same direction. Such an arrangement of light source and detecting device on one and the same circuit board can be manufactured in a particularly easy manner. To give an example, the light source can emit light in upward direction. The detecting device can detect light being radiated onto it from an upward direction. Such an arrangement makes use of light guided on a bow-like beam path. This can be achieved in a particularly simple manner if a fitting as described above is provided on a main body of the holding device. Then, the light can be emitted from the light source and can be guided through the fitting towards the main body of the holding device. Afterwards, it is radiated along a coding structure of a breathing tube inserted into the holding device and afterwards guided through the holding device and an optional lens towards the detecting device. Thus, the fitting which is present on the holding device in an embodiment of the lung function diagnostics device makes any angled arrangements of light source and detecting device superfluous. It allows for easy placement of the holding device of the lung function diagnostics device directly above the circuit board. It is not necessary that the circuit board comprises any specific arrangements for emitting light in a specific direction. Rather, light emitted such that a line extending along the light emission direction in the center of a light emitting cone is arranged approximately perpendicular to a plane in which the circuit board extends can well be used for operating the lung function diagnostics device.

The light source can be an individual light source or a plurality (at least two) of light sources arranged next to each other, such as a light source array. Light emitting diodes (LEDs) are particularly appropriate light sources.

In an embodiment, the detecting device is a line detector comprising a plurality of individual detectors or an array of detectors so that irradiating a specific area can be detected well by the detecting device.

So far, holding devices for breathing tubes for lung function diagnostics have not been manufactured from selectively transparent materials according to the knowledge of the inventors. This can be easily explained by the fact that evidence is not available of using light having a specific wavelength for reading out a coding on a breathing tube to be inserted into the holding device and to minimize the influence of scattered light within lung function diagnostics devices. Therefore, in an aspect, the instant disclosure also relates to the novel use of a material that is transparent for light having a wavelength in a first wavelength range but nontransparent for light having a wavelength in a second wavelength range for manufacturing a holding device for a breathing tube for use in lung function diagnostics. In an embodiment, the manufactured holding device fully consists of the selectively transparent material.

In an aspect, the instant disclosure also relates to a method for reading out a coding on the surface of a breathing tube for use in lung function diagnostics. This method comprises the following steps.

In a first step, a breathing tube is placed into the holding device. Thereby, the holding device comprises a selectively transparent material, i.e., a material that is transparent for light having a wavelength in a first wavelength range but nontransparent for light having a wavelength in a second wavelength range.

Afterwards, light having a wavelength within the first wavelength range is radiated through the holding device onto the breathing tube in a region in which a coding is arranged on the breathing tube.

Afterwards, the light that has passed the coding of the breathing tube is detected with a detecting device.

Thereby, the coding can be embodied by a comb-like structure on the surface of the breathing tube. Then, the light detected by the detecting device comprises a shadow pattern produced by the comb-like structure. Based on the specific shadow pattern detected by the detecting device, the coding is read out. Then, the position of the breathing tube within the holding device is determined on the basis of the position of the shadow pattern. Alternatively or additionally, the breathing tube in question is identified (i.e., the type of breathing tube is identified) on the basis of the shadow pattern and therewith on the basis of the coding of the breathing tube.

In an embodiment, the light is emitted by the light source in a first direction and is then guided through the holding device so that it exits the holding device in a second direction. Thereby, an angle between the first line extending along the first direction and a second line extending along the second direction is in a range of from 0° to 60°, in particular from 5° to 55°, in particular from 10° to 50°, in particular from 15° to 45°, in particular from 20° to 40°, in particular from 25° to 35°, in particular from 30° to 55°. By such an angled guiding of the light through the holding device, it is possible to scan the coding structure of the breathing tube inserted into the holding device and to detect the light by the detecting device that is arranged in the same plane as the light source. To give an example, both the light source and the detecting device can be arranged on a planar circuit board.

In an embodiment, the light is emitted by the light source in a first direction towards the fitting extending away from a lateral portion of the main body of the holding device.

Thereby, the light is reflected within the fitting at least once prior to entering the main body in a third direction. Thereby, an angle between a first line extending along the first direction and a third line extending along the third direction is in a range of from 30° to 90°, in particular from 35° to 85°, in particular from 40° to 80°, in particular from 45° to 75°, in particular from 50° to 70°, in particular from 55° to 65°, in particular from 60° to 90°. Such an angled guiding of a light beam through the fitting serves for a particularly appropriate coupling of the light beam into the main body of the holding device so that the light can pass through the main body of the holding device towards a coding region of a breathing tube inserted into the holding device. Thereby, it is not necessary to arrange the light source remote from the circuit board of the lung function diagnostics device in a specific angle with respect to the holding device. Rather, it is possible to arrange the light source on the same circuit board as the detecting device, thus making it particularly easy to manufacture a corresponding lung function diagnostics device and to carry out the precedingly described method.

Embodiments described with respect to the holding device, to the lung function diagnostics device, to the novel use of a selectively transparent material and to a method for reading out a coding on a surface of a breathing tube can be combined in any desired way and can be transferred from the holding device to the lung function diagnostics device, to the use of a selectively transparent material and to the method for reading out a coding on the surface of the breathing tube, and vice versa. The summary provided above is to aid in understanding the embodiments of the disclosure and is not limiting.

BRIEF DESCRIPTION OF THE DRAWINGS

Further details and aspects of embodiments of the instant disclosure will be explained with respect to exemplary embodiments and accompanying Figures.

FIG. 1E shows a view of the left side of the breathing tube holder of FIG. 1A.

FIG. 1F shows a cross-sectional view of the breathing tube holder of FIG. 1A along the line A-A indicated in FIG. 1B.

FIGS. 1-4 are shown approximately to scale.

DETAILED DESCRIPTION

Figure 1A:
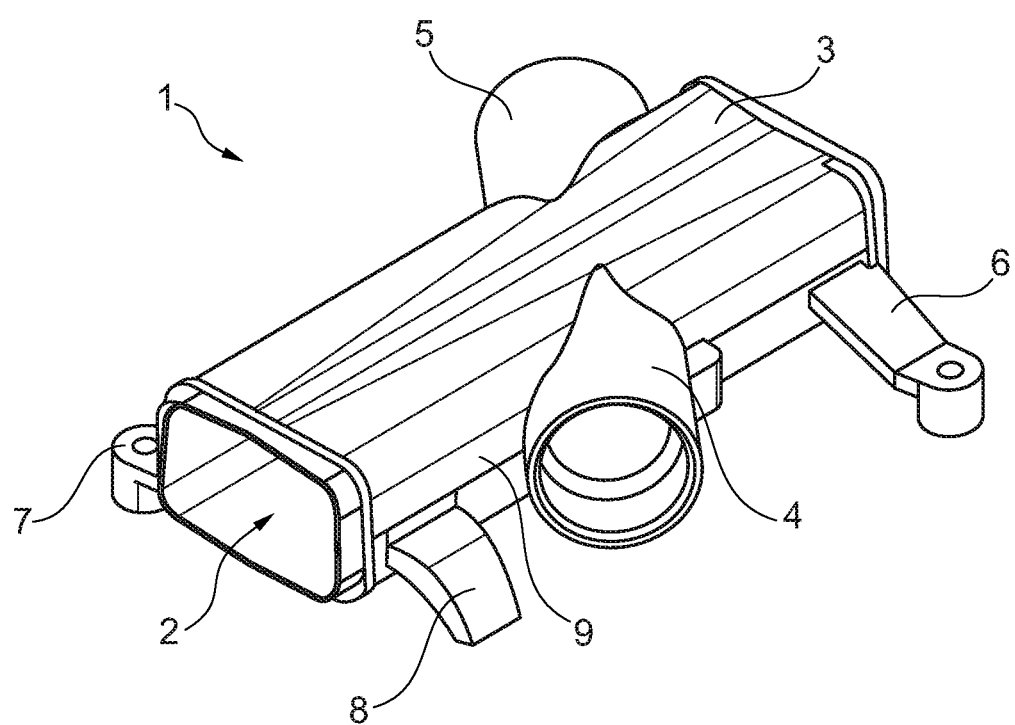
FIG. 1A shows a perspective view on an embodiment of a breathing tube holder.

FIG. 1A shows a perspective view of a breathing tube holder 1 as holding device for a breathing tube for use in lung function diagnostics. This breathing tube holder 1 comprises an inner breathing tube space 2 into which a breathing tube (not shown in FIG. 1A) can be inserted for lung function diagnostics and can be removed after use. The inner breathing tube space 2 serves as an inner main space of the breathing tube holder 1. It is defined by a main body 3 of the breathing tube holder 1.

On a first side of the main body 3, a first ultrasonic transceiver housing 4 is arranged. On a second side, which is opposite to the first side, a second ultrasonic transceiver housing 5 is arranged. The first ultrasonic transceiver housing 4 can also be denoted as first side body. The second ultrasonic transceiver housing 5 can also be denoted as second side body. When the breathing tube holder 1 is in operation, one ultrasonic transceiver is inserted into the first ultrasonic transceiver housing 4 and a second ultrasonic transceiver is inserted into the second ultrasonic transceiver housing 5.

The breathing tube holder 1 further comprises a first flange 6 and a second flange 7 which serve for mounting the breathing tube holder 1 into a lung function diagnostics device.

A light guiding fitting 8 is integrally formed with the main body 3 of the breathing tube holder 1 on a first side 9 of the main body 3. Thereby, the light guiding fitting 8 extends away from this first side 9 in a curved manner. This light guiding fitting 8 serves for guiding infrared light through the breathing tube holder 1 onto a breathing tube that is inserted into the inner breathing tube space 2. This will be explained in the following in more detail.

Figure 1B:
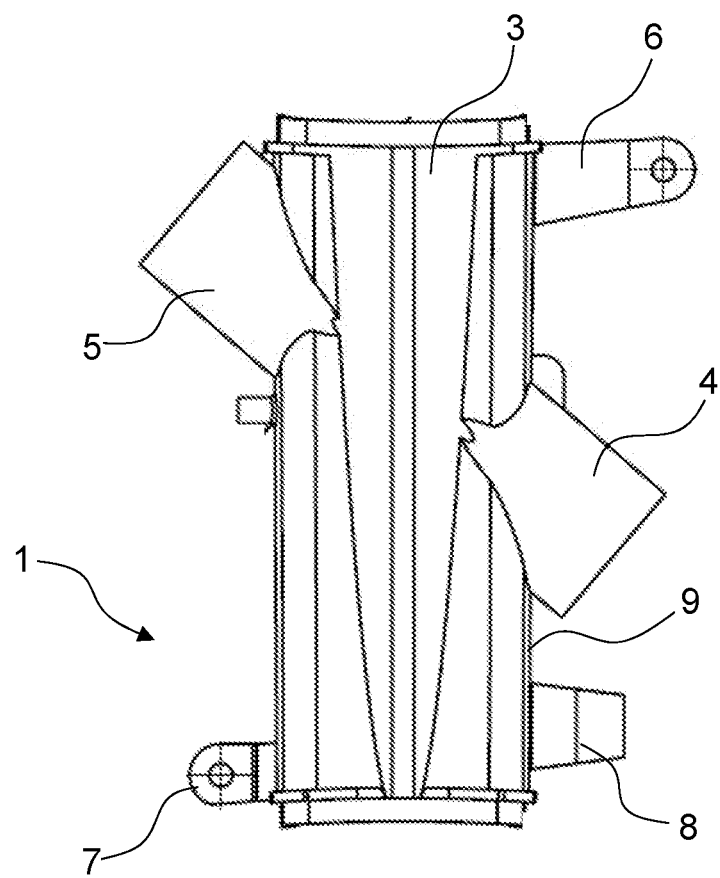
FIG. 1B shows a top view onto the breathing tube holder of FIG. 1A.

FIG. 1B shows a top view onto the breathing tube holder 1 of FIG. 1A. Thereby, in this and following FIGs, the same elements will be referred to with the same numeral references. Regarding the details of FIGS. 1B to 1F, reference is made to the explanations given with respect to FIG. 1A. In the following, only specific details that are not well visible in FIG. 1A will be explained.

Figure 1C:
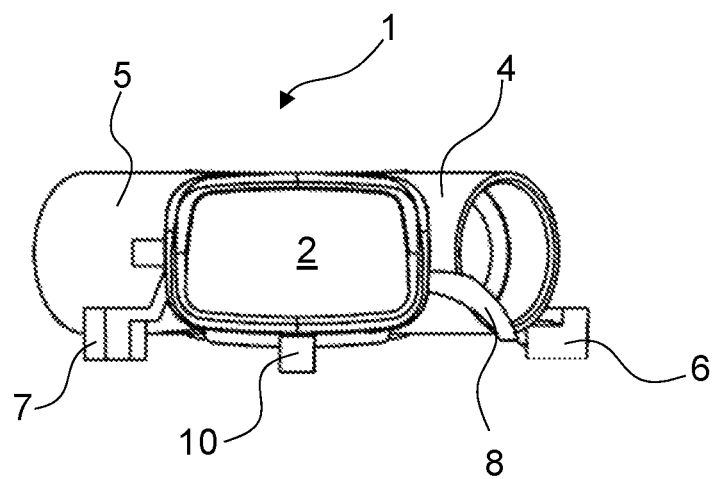
FIG. 1C shows a front view of the breathing tube holder of FIG. 1A.

FIG. 1C shows a front view of the breathing tube holder 1 of FIG. 1A. Thereby, a supporting extension 10 arranged on a lower side of the breathing tube 14 can be seen. This supporting extension 10 serves for supporting the breathing tube 14 in its installed state.

Figure 1D:
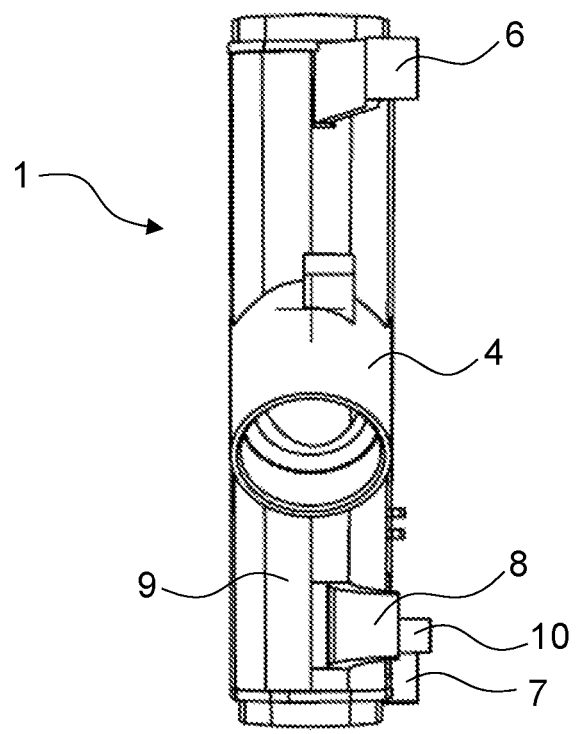
FIG. 1D shows a view of the right side of the breathing tube holder of FIG. 1A.

FIG. 1D shows a lateral view of the breathing tube holder 1 of FIG. 1A from the right side as shown in FIG. 1A.

FIG. 1E shows a lateral view of the breathing tube holder 1 from the left side as shown in FIG. 1A.

FIG. 1F shows a cross-sectional view along the line A-A in FIG. 1E of the breathing tube holder 1. Thereby, it can be seen that a first ultrasonic transceiver receiving space 40 is provided within the first ultrasonic transceiver housing 4. Likewise, a second ultrasonic transceiver receiving space 50 is provided within the second ultrasonic transceiver housing 5.

Figure 2A:
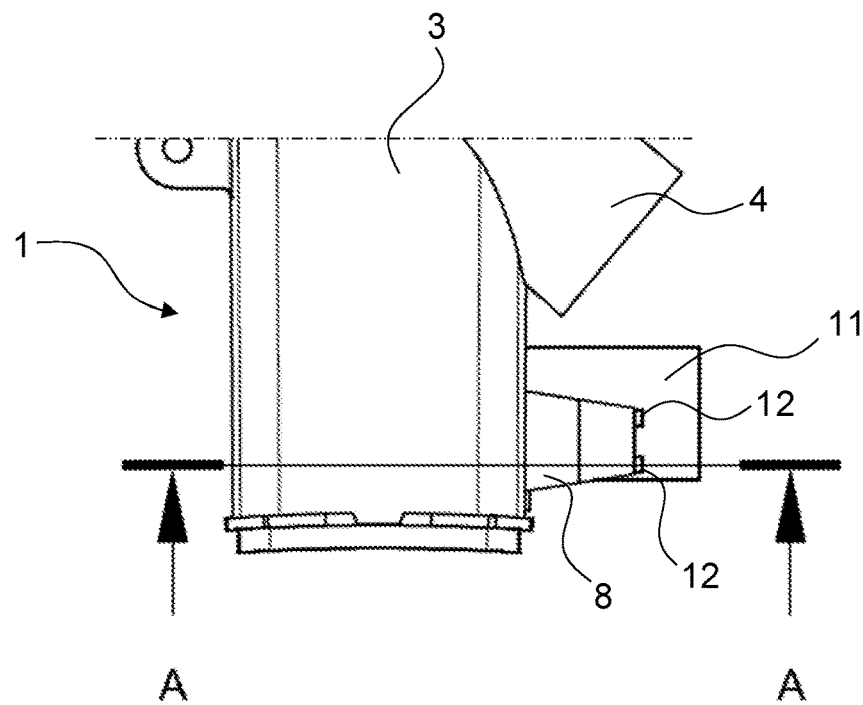
FIG. 2A shows a detailed view of an arrangement of a breathing tube holder and a circuit board located under the breathing tube holder.

FIG. 2A shows a detailed view of a breathing tube holder 1 (together with its already explained components) and a schematically illustrated circuit board 11. Thereby, two infrared light emitting diodes (LEDs) 12 are arranged on the circuit board 11. In one embodiment, these infrared LEDs 12 emit light at a wavelength of 860 nm with a spectral width of 30 nm.

Figure 2B:
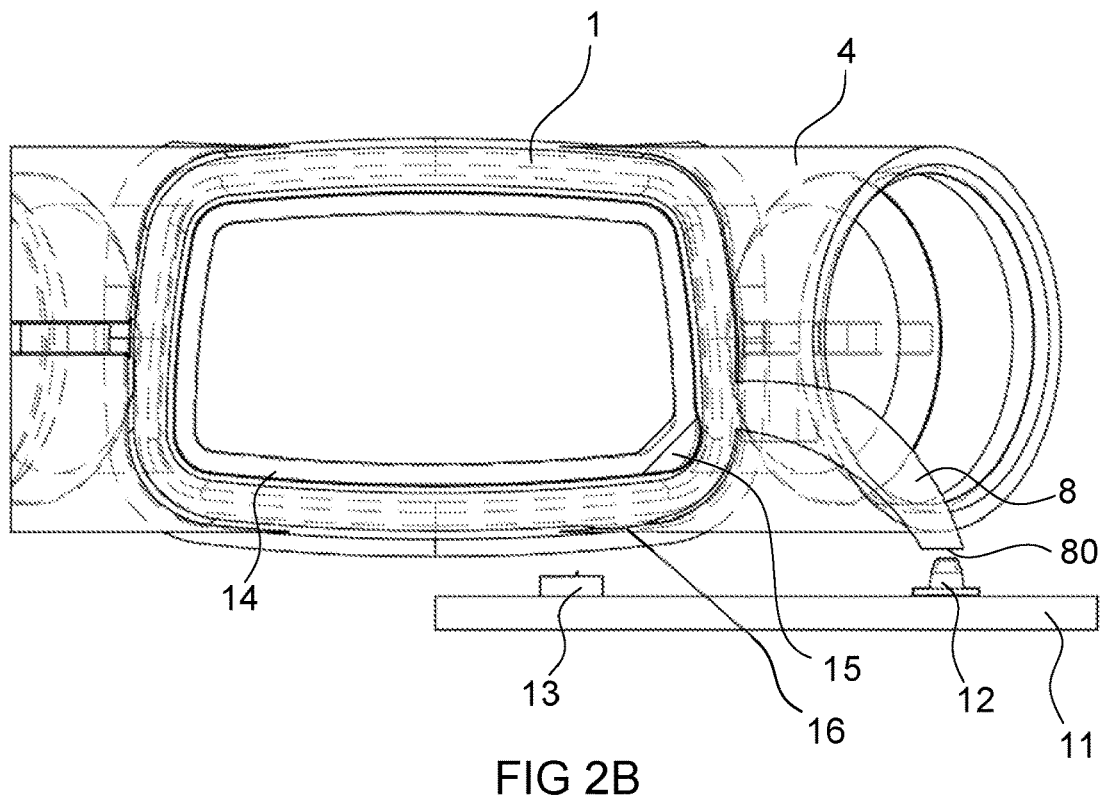
FIG. 2B shows a cross-sectional view through the arrangement of FIG. 2A along the line A-A indicated in FIG. 2A.

FIG. 2B shows the arrangement of FIG. 2A in a partial cross-sectional view along the line A-A indicated in FIG. 2A. Thereby, FIG. 2B illustrates in addition to one of the infrared LEDs 12 an infrared line detector 13 as detecting device arranged on the circuit board 11. The infrared LEDs 12 as well as the infrared detector 13 face in the same direction, namely upwards, as shown in FIG. 2B.

A breathing tube 14 is inserted into the inner breathing tube space 2 of the breathing tube holder 1. This breathing tube 14 comprises a coding in form of a comb-like structure 15 that is arranged on an outer edge of the breathing tube 14. The breathing tube holder 1 of FIG. 2B additionally comprises a lens 16 that is formed on a lower side of the main body of the breathing tube holder 1 as integral part of the breathing tube holder 1.

A free end 80 of the light guiding fitting 8 directly faces the infrared LEDs 12. Thereby, this free end 80 is arranged on a plane which is parallel to a plane, of which the circuit board 11 is a part (the circuit board 11 extends in the latter plane). In addition, the lens 16 faces towards the plane in which the free end 80 of the light guiding fitting 8 extends.

Figure 3:
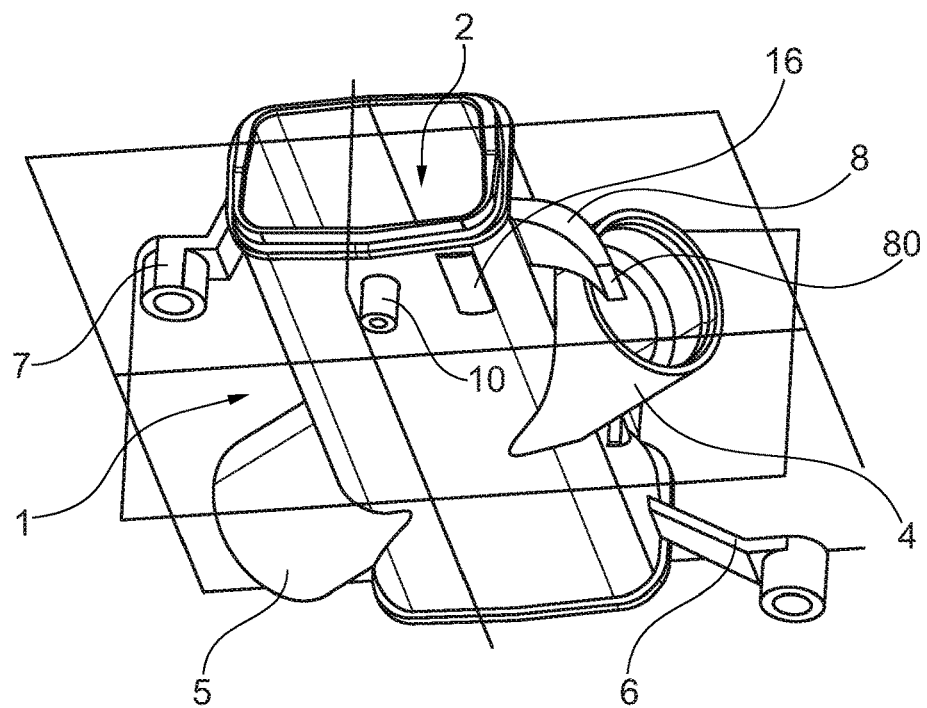
FIG. 3 shows a view of the bottom of an embodiment of a breathing tube holder.

FIG. 3 shows a view from the bottom side onto the breathing tube holder 1 of FIGS. 2A and 2B without breathing tube and without circuit board. In this view, the lens 16 arranged on the bottom of the main body of the breathing tube holder 1 as well as a flat free end 80 serving as light entrance plane of the light guiding fitting 8 are visualized in dark color for highlighting purposes. As will be explained in the following with respect to FIG. 4, light enters into the breathing tube holder 1 via the free end 80 of the light fitting guiding 8 and exits the breathing tube holder 1 through the lens 16. Thus, both light entrance into the breathing tube holder 1 as well as light exit from the breathing tube holder 1 occurs on the same side of the breathing tube holder 1.

Figure 4:
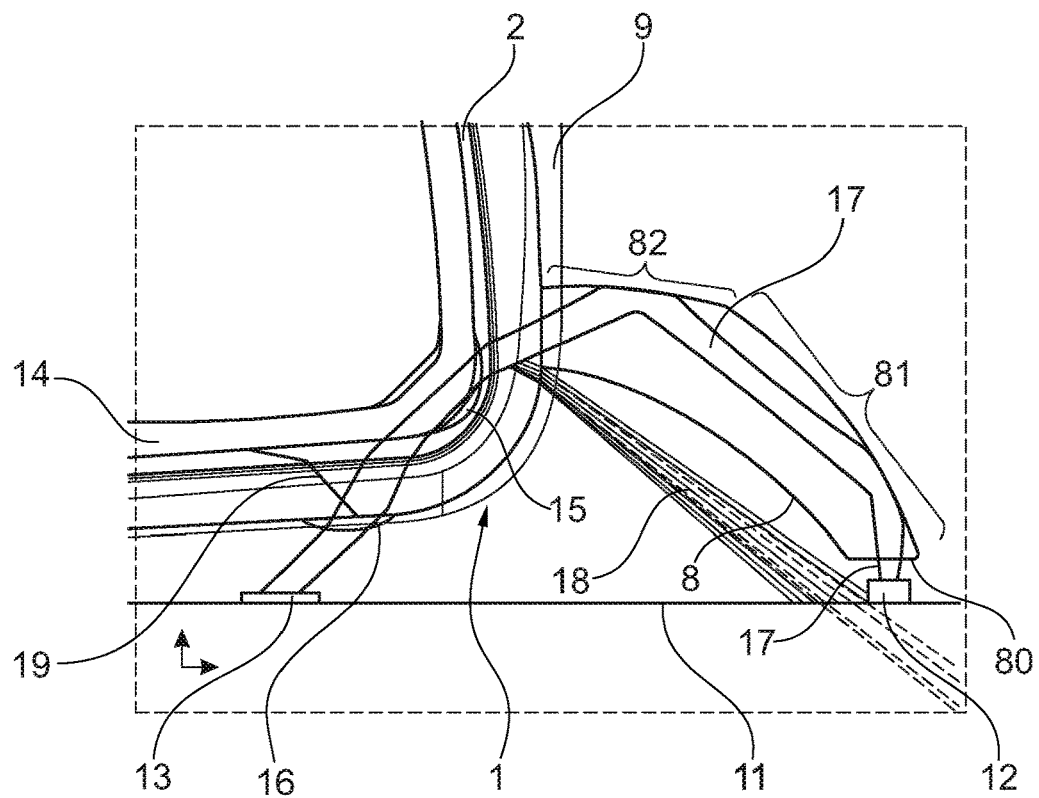
FIG. 4 shows a cross-sectional view of the breathing tube holder of FIG. 3 with illustrated light beam guiding.

This is illustrated in more detail in FIG. 4 showing a cross-sectional view of the breathing tube holder 1 illustrated in the preceding FIGs in the area of the light guiding fitting 8. Thereby, also the circuit board 11 is schematically illustrated.

In operation, infrared light is emitted by two infrared LEDs 12 and enters the light guiding fitting 8 through its free end 80. The infrared light 17 is then reflected on an inner surface of the light guiding fitting 8 in a first section 81 of the light fitting guiding 8. The infrared light is then further guided through the light guiding fitting 8 towards an inner surface of a second section 82 of the light guiding fitting 8 and is once again reflected. Thereby, the curvature of the first section 81 is different from the curvature of the second section 82 of the light guiding fitting 8. The infrared light 17 is then guided through the first side 9 of the breathing tube holder 1 into the inner breathing tube space 2 of the breathing tube holder 1. There, the infrared light 17 hits a comb-like structure 15 of the breathing tube 14 that is inserted into the breathing tube holder 1. A part of the infrared light 17 is reflected upon exiting the first side 9 of the breathing tube holder 1 to the inner breathing tube space 2 of the breathing tube holder 1. This first reflected infrared light 18 is reflected back in the direction of the infrared LEDs 12 (i.e. it is reflected towards the infrared LEDs).

The infrared light beam 17 then passes the comb-like structure 15 on the exterior of the breathing tube 14 and enters again the breathing tube holder 1. It then passes the lens 16 and finally exits the breathing tube holder 1. Thereby, the infrared light 17 is focused onto the infrared detector 13 which is arranged on the circuit board 11. Upon finally exiting the breathing tube holder 1, a second part of the infrared light 17 is reflected back towards the inner breathing tube space 2 of the breathing tube holder 1. This second reflected infrared light 19 generally makes up a smaller part of the reflected infrared light than the first reflected infrared light 18.

Since the comb-like structure 15 generates a shadow pattern upon being irradiated with infrared light 17, a corresponding shadow pattern can be detected by detector 13. Thereby, it can be determined whether or not the breathing tube 14 is inserted into the breathing tube holder 1, i.e., its position within the breathing tube holder 1 is detected. Furthermore, the type of breathing tube 14 can be detected by the shadow pattern. Such a lung function diagnostics device might reject a specific test if a breathing tube 14 is used that is not intended to be used for this test.

A line extending along the direction of emission of the infrared light 17 from the infrared LEDs 12 and a line extending along the direction of the infrared light 17 being focused from the lens 16 towards the detector 13 intersect each other at an angle of approximately 50° in one embodiment.

A line extending along the direction of emission of the infrared light 17 from the infrared LEDs 12 and a line extending in the direction of the infrared light 17 passing through the first side 9 of the breathing tube holder 1 intersect each other at an angle of approximately 65° in the embodiment.

These angles are to be understood only exemplarily since they strongly depend on the dimensions and the curvature of the light guiding fitting 8 and the optical properties of the lens 16. The infrared light 17 can also be guided through the breathing tube holder 1 under different angles without deviating from the scope of the instant disclosure. However, it turned out to be most convenient if the infrared LEDs 12 and the detector 13 face in the same direction and are arranged on the circuit board 11 in approximately the same plane. Thus, the instantly described breathing tube holder 1 makes it possible that complicated arrangements of infrared LEDs and infrared detectors are not necessary for emitting infrared light and properly detecting it after it has passed the coding region of a breathing tube like the comb-like structure 15 of breathing tube 14.

FIGS. 1-4 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. The term approximately is construed to mean plus or minus five percent of the stated values unless otherwise specified. Such claims, whether broader, narrower, equal, or different in scope to the original claims, also are regarded as included within the subject matter of the present disclosure.

What claimed is:

1. A holding device for a breathing tube for use in a lung function diagnostic application, the holding device entirely consisting of a material that is transparent for light having a wavelength in a first wavelength range but nontransparent for light having a wavelength in a second wavelength range,
   the holding device further comprising a fitting extending away from a lateral portion of a main body of the holding device, wherein the fitting has a free end arranged in a first plane parallel to a second plane of which a circuit board is a part, wherein the fitting extends at an angle of 30° to 120° to a third plane in which the lateral portion of the main body extends,
   wherein the fitting guides, in an interior of the fitting, a light beam emitted from a light source on the circuit board towards and through the main body of the holding device onto a detecting device on the circuit board such that a direction of the light beam is changed within the fitting, and wherein the light source and the detecting device face in a same direction.

2. The holding device according to claim 1, wherein the first wavelength range comprises wavelengths of at least 600 nm.

3. The holding device according to claim 1, wherein the first wavelength range has a spectral width of not more than 200 nm.

4. The holding device according to claim 1, wherein the second wavelength range comprises wavelengths of less than 600 nm.

5. The holding device according to claim 1, wherein the second wavelength range has a spectral width of at least 200 nm.

6. The holding device according to claim 1, wherein the material comprises at least one base material chosen from the group consisting of polycarbonates, acrylonitrile butadiene styrene, polystyrene, poly(methyl methacrylate), polyethylene terephthalate, polyethylene terephthalate glycol, copolymers of polystyrene and polyethylene terephthalate glycol, cellulose esters such as cellulose acetate butyrate, and copolymers of these base materials.

7. The holding device of claim 1 further comprising a lens formed on a lower side of the holding device, wherein the lens faces towards the first plane in which the free end of the fitting extends.

8. A holding device for a breathing tube, the holding device consisting of a material that is transparent for light having a wavelength in a first wavelength range but nontransparent for light having a wavelength in a second wavelength range; and the holding device comprising:
   a main body surrounding an inner main space which serves for removably housing a breathing tube for use in a lung function diagnostic application chosen from the group consisting of spirometry, gas washout measurements, gas dilution measurements, and gas diffusion measurements, a first side body extending laterally from the main body on a first side, and a second side body extending laterally from the main body on a second side being opposite to the first side, wherein the first side body surrounds a first inner side space and the second side body surrounds a second inner side space, wherein the first inner side space serves for housing a first ultrasonic transceiver and the second inner side space serves for housing a second ultrasonic transceiver,
   a fitting extending away from a lateral portion of the main body of the holding device, wherein the fitting has a free end arranged in a first plane parallel to a second plane of which a circuit board is a part, wherein the fitting extends at an angle of 30° to 120° to a third plane in which the lateral portion of the main body extends,
   wherein the fitting guides, in an interior of the fitting, a light beam emitted from a light source on the circuit board towards and through the main body of the holding device onto a detecting device on the circuit board such that a direction of the light beam is changed within the fitting, and wherein the light source and the detecting device face in a same direction.

9. The holding device according to claim 8, wherein the light is infrared light.

10. The holding device according to claim 8, wherein the fitting guides the light along a coding structure of a breathing tube inserted into the holding device.

11. The holding device according to claim 8, wherein the fitting has a curved surface.

12. The holding device according to claim 11, wherein the curved surface comprises at least two sections having different curvatures.

13. The holding device according to claim 8, wherein the holding device comprises a lens being integrally formed as part of a surface of the holding device, wherein the lens faces towards the first plane in which the free end of the fitting extends.

14. A lung function diagnostics device, including a holding device, the holding device entirely consisting of a material that is transparent for light having a wavelength in a first wavelength range but nontransparent for light having a wavelength in a second wavelength range,
   the holding device further comprising a fitting extending away from a lateral portion of a main body of the holding device, wherein the fitting has a free end arranged in a first plane parallel to a second plane of which a circuit board is a part, wherein the fitting extends at an angle of 30° to 120° to a third plane in which the lateral portion of the main body extends,
   wherein the fitting guides, in an interior of the fitting, a light beam emitted from a light source on the circuit board towards and through the main body of the holding device onto a detecting device on the circuit board such that a direction of the light beam is changed within the fitting, wherein the light source and the detecting device face a same direction, and
   wherein the lung function device performs at least one of spirometry measurements, gas washout measurements, gas dilution measurements, and gas diffusion measurements.

15. The lung function diagnostics device according to claim 14, wherein the light source emits light having a wavelength in a first wavelength range and the detecting device detects light having a wavelength in the first wavelength range.

16. A method for reading out a coding on a surface of a breathing tube for use in lung function diagnostics, comprising the following steps:
   a) placing the breathing tube into a holding device, wherein the holding device entirely consists of a material transparent for light having a wavelength in a first wavelength range but nontransparent for light having a wavelength in a second wavelength range,
   the holding device further comprising a fitting extending away from a lateral portion of a main body of the holding device, wherein the fitting has a free end arranged in a first plane parallel to a second plane of which a circuit board is a part, wherein the fitting extends at an angle of 30° to 120° to a third plane in which the lateral portion of the main body extends,
   b) irradiating light having a wavelength in the first wavelength range emitted by a light source on a circuit board appropriate to emit light having a wavelength in the first wavelength range through the holding device onto the breathing tube in a region in which a coding is arranged on the breathing tube,
   c) detecting the light that has passed the coding of the breathing tube with a detecting device on the circuit board, wherein the light source and the detecting device face a same direction.

* * * * *